(12) United States Patent
Sterling et al.

(10) Patent No.: US 7,215,987 B1
(45) Date of Patent: May 8, 2007

(54) METHOD AND APPARATUS FOR PROCESSING SIGNALS REFLECTING PHYSIOLOGICAL CHARACTERISTICS

(75) Inventors: Bernhard B. Sterling, Danville, CA (US); Alexander K. Mills, San Antonio, CA (US)

(73) Assignee: Woolsthorpe Technologies, Brentwood, TN (US)

( * ) Notice: Subject to any disclaimer, the term of this patent is extended or adjusted under 35 U.S.C. 154(b) by 31 days.

(21) Appl. No.: 11/270,241

(22) Filed: Nov. 8, 2005

(51) Int. Cl.
*A61B 5/00* (2006.01)

(52) U.S. Cl. ...................................... 600/336; 600/322
(58) Field of Classification Search ................ 600/310, 600/322, 323, 336
See application file for complete search history.

(56) References Cited

U.S. PATENT DOCUMENTS

| | | | |
|---|---|---|---|
| 4,934,372 A | 6/1990 | Corenman et al. | |
| 5,482,036 A * | 1/1996 | Diab et al. | 600/364 |
| 5,490,505 A | 2/1996 | Diab et al. | |
| 6,036,642 A | 3/2000 | Diab et al. | |
| 6,157,850 A | 12/2000 | Diab et al. | |
| 6,206,830 B1 | 3/2001 | Diab et al. | |
| 6,263,222 B1 | 7/2001 | Diab et al. | |
| 6,480,729 B2 | 11/2002 | Stone | |
| RE38,492 E | 4/2004 | Diab et al. | |
| 2004/0068164 A1 | 4/2004 | Diab et al. | |

\* cited by examiner

*Primary Examiner*—Eric Winakur
*Assistant Examiner*—Etsub Berhanu
(74) *Attorney, Agent, or Firm*—Francis Law Group

(57) ABSTRACT

The invention comprises a method and apparatus for processing signals reflecting a physiological characteristic by detecting the intensity of light following tissue absorption at two wavelengths and subtracting the best estimate of the desired signal from the difference between the signals. Corrected first and second intensity signals are determined by applying a residual derived from a combination of the first and second intensity signals as multiplied by a residual factor and subtracted from a difference between the first and second intensity signals to the first and second intensity signals. In one embodiment, the method and apparatus are used to determine arterial oxygen saturation.

23 Claims, 8 Drawing Sheets

METHOD AND APPARATUS FOR PROCESSING SIGNALS REFLECTING PHYSIOLOGICAL CHARACTERISTICS

FIELD OF THE PRESENT INVENTION

The present invention relates to the field of signal processing. More specifically, the invention relates to a method for processing signals reflecting physiological characteristics.

BACKGROUND OF THE INVENTION

Physiological monitoring systems and apparatus, which are adapted to acquire signals reflecting physiological characteristics, are well known in the art. The physiological characteristics include, for example, heart rate, blood pressure, blood gas saturation (e.g., oxygen saturation) and respiration rate.

The signals acquired by the noted physiological monitoring systems and apparatus are however composite signals, comprising a desired signal portion that directly reflects the physiological process that is being monitored and an undesirable signal portion, typically referred to as interference or noise. The undesirable signal portions often originate from both AC and DC sources. The DC component, which is easily removed, results from the transmission of energy through differing media that are of relatively constant thickness within the body (e.g., bone, tissue, skin, blood, etc.).

Undesirable AC components of the acquired signal correspond to variable or erratic noise and interference, and thus have been conventionally quite difficult to characterize and remove.

One example of a physiological monitoring apparatus, wherein the measured signal can, and in many instances will, include undesirable signal components, is a pulse oximeter.

Pulse oximeters typically measure and display various blood constituents and blood flow characteristics including, but not limited to, blood oxygen saturation of hemoglobin in arterial blood, the volume of individual blood pulsations supplying the flesh and the rate of blood pulsations corresponding to each heartbeat of the patient. Illustrative are the apparatus described in U.S. Pat. Nos. 5,193,543; 5,448,991; 4,407,290; and 3,704,706.

As is well known in the art, a pulse oximeter passes light through human or animal body tissue where blood perfuses the tissue, such as a finger, an ear, the nasal septum or the scalp, and photoelectrically senses the absorption of light in the tissue. The amount of light absorbed is then used to calculate the amount of blood constituent being measured.

Two lights having discrete frequencies in the range of about 650–670 nanometers in the red range and about 800–1000 nanometers in the infrared range are typically passed through the tissue. The light is absorbed by the blood in an amount representative of the amount of the blood constituent present in the blood. The amount of transmitted light passed through the tissue varies in accordance with the changing amount of blood constituent in the tissue and the related light absorption.

The output signal from the pulse oximeter, which is sensitive to the arterial blood flow, contains a component that is a waveform representative of the patient's blood gas saturation. This component is referred to as a "plethysmographic wave or waveform" (see curve P in FIG. 1).

The plethysmograph signal (and the optically derived pulse rate) may however be subject to irregular variants that interfere with the detection of the blood constituents. The noise, interference and other artifacts can, and in many instances will, cause spurious pulses that are similar to pulses caused by arterial blood flow. These spurious pulses, in turn, may cause the oximeter to process the artifact waveform and provide erroneous data.

Several signal processing methods (and apparatus) have been employed to reduce the effects of undesirable signal components on the measured signal and, hence, the derived plethysmograph waveform. Illustrative are the methods and apparatus disclosed in U.S. Pat. No. 4,934,372, which correlate a subject's electrocardiogram waveform with the acquired signal to identify desired portions of the signal to more accurately detect blood constituents.

Similarly, U.S. Pat. Nos. 5,490,505, 6,036,642, 6,206,830, and 6,263,222, all disclose signal processors that generate either a noise reference or a signal reference which is used to drive a correlation canceler and generate a waveform that approximates either the desired or undesired component of the acquired signal. A primary intended application of the noted signal processors is the measurement of blood oxygen saturation in a manner that minimizes the effect of motion artifacts. However, a consequence of the process used to generate the reference is that a third optical signal must be acquired to provide ratiometric calculation of saturation.

Accordingly, each of the noted prior art references require the acquisition of additional signals to help measure blood oxygen saturation. As such, these systems are inherently more complex and costly. Further, the noted references are primarily concerned with filtering out motion artifacts. Therefore, these references are not tailored to the removal of undesired signal components that arise from other sources.

It is therefore an object of the present invention to provide a cost effective, reliable means of determining a physiological characteristic by detecting a minimum number of signals.

It is another object of the invention to provide a method for processing signals reflecting a physiological characteristic that does not require correlation canceling.

Another object of the invention is to provide a method for processing signals reflecting a physiological characteristic that minimizes undesirable signal components.

It is yet another object of the invention to provide a method and apparatus for correcting signals reflecting a physiological characteristic that does not require a pulse waveform model or data from preceding pulse waveforms.

Yet another object of the invention is to provide a method and apparatus for correcting signals reflecting a physiological characteristic using data from a single pulse.

A further object of the invention is to provide a method and apparatus for determining arterial oxygen saturation with improved accuracy.

It is another object of the invention to provide a method for processing oximetry signals based on specific time dependent differences during a single pulse.

Another object of the invention is to provide a method for improving an oximetry signal based on analytical, mathematical steps that are analytically transparent, interpretable and adjustable on a physiological and physical level, and based on an understanding of the variables that interfere with oximetry signals, to optimally minimize specific interferences with the oximetry signal.

SUMMARY OF THE INVENTION

In accordance with the above objects and those that will be mentioned and will become apparent below, the invention includes a device for the monitoring of a physiological characteristic of a patient's blood, having first and second radiation emitters that emit light at first and second wavelengths, a radiation detector configured to receive light at the first and second wavelengths after absorbance through the patient's blood and provide first and second intensity signals corresponding to the first and second received wavelengths, and a controller for computing the physiological characteristic of the patient's blood from a corrected first and second intensity signal determined by applying a residual derived from a combination of the first and second intensity signals as multiplied by a residual factor and subtracted from a difference between the first and second intensity signals to the first and second intensity signals.

In one embodiment, the device is configured to determine arterial oxygen saturation.

Preferably, the first wavelength is in the range of approximately 650–670 nm. Also preferably, the second wavelength is in the range of 800–1000 nm.

In one aspect of the invention, the residual factor is determined by minimizing the absolute value of the difference between the residual at a time midpoint and an average of the residual at a first data minimum and at a first data maximum. In another aspect of the invention, the residual factor is determined by minimizing the absolute value of the difference of the residual at a first data maximum and the residual at a first data minimum. Preferably, the residual factor is determined by minimizing both values. Also preferably, the first data minimum and the first data maximum are determined by polynomial fitting.

In another embodiment of the invention, the residual factor is related to reference oxygen saturation to determine the physiological characteristic.

In yet another embodiment of the invention, a ratio of the corrected intensity signals is related to reference oxygen saturation to determine the physiological characteristic.

According to one embodiment of the invention, the residual is substantially free of signal related to the physiological characteristic.

In another embodiment, the residual substantially corresponds to undesirable signal components.

The invention also comprises a method for processing signals reflecting a physiological characteristic of a patient's blood, comprising the steps of (i) coupling an oximeter sensor arrangement to a tissue region of the patient; (ii) passing first and second lights through the patient's tissue region, wherein the first light is substantially in a red light range and the second light is substantially in an infrared light range; (iii) detecting the first and second lights absorbed by the tissue region and providing a first and second intensity signal corresponding to the absorbed first and second lights; and (iv) computing the physiological characteristic of the patient's bl ood from a corrected first and second intensity signal determined by applying a residual derived from a combination of the first and second intensity signals as multiplied by a residual factor and subtracted from a difference between the first and second intensity signals to the first and second intensity signals. Preferably, the physiological characteristic determined is arterial oxygen saturation.

In the noted embodiment, the residual factor is preferably determined by minimizing the absolute value of the difference between the residual at a time midpoint and an average of the residual at a first data minimum and at a first data maximum. Also preferably, the residual factor is determined by minimizing the absolute value of the difference of the residual at a first data maximum and the residual at a first data minimum. Most preferably, the residual factor is determined by minimizing both values.

According to one aspect of the invention, the residual factor is related to reference oxygen saturation to determine the physiological characteristic. In another embodiment, a ratio of the corrected intensity signals is related to reference oxygen saturation to determine the physiological characteristic.

In one embodiment of the invention, the residual factor is determined by minimizing a qualifier. Preferably, the qualifier is selected to correspond to the physiological characteristic.

In a further embodiment, the invention comprises a method for determining a patient's arterial oxygen saturation comprising the steps of i) coupling an oximeter sensor arrangement to a tissue region of the patient, ii) passing first and second lights through the patient's tissue region, wherein the first light is substantially in a red light range and the second light is substantially in an infrared light range, iii) detecting the first and second lights absorbed by the tissue region and providing a first intensity signal and a second intensity signal corresponding to the absorbed first and second lights, and iv) computing the arterial oxygen saturation of the patient's blood from a corrected first intensity signal and a corrected second intensity signal determined by applying a residual derived from a combination of the first and second intensity signals as multiplied by a residual factor and subtracted from a difference between the first and second intensity signals to the first and second intensity signals, wherein the residual factor is determined by minimizing the absolute value of the difference between the residual at a first timepoint of a pulse corresponding to a time midpoint and an average of the residual at a second timepoint of the pulse corresponding to a first data minimum and at a third timepoint of the pulse corresponding to a first data maximum.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE INVENTION

Figure 1:
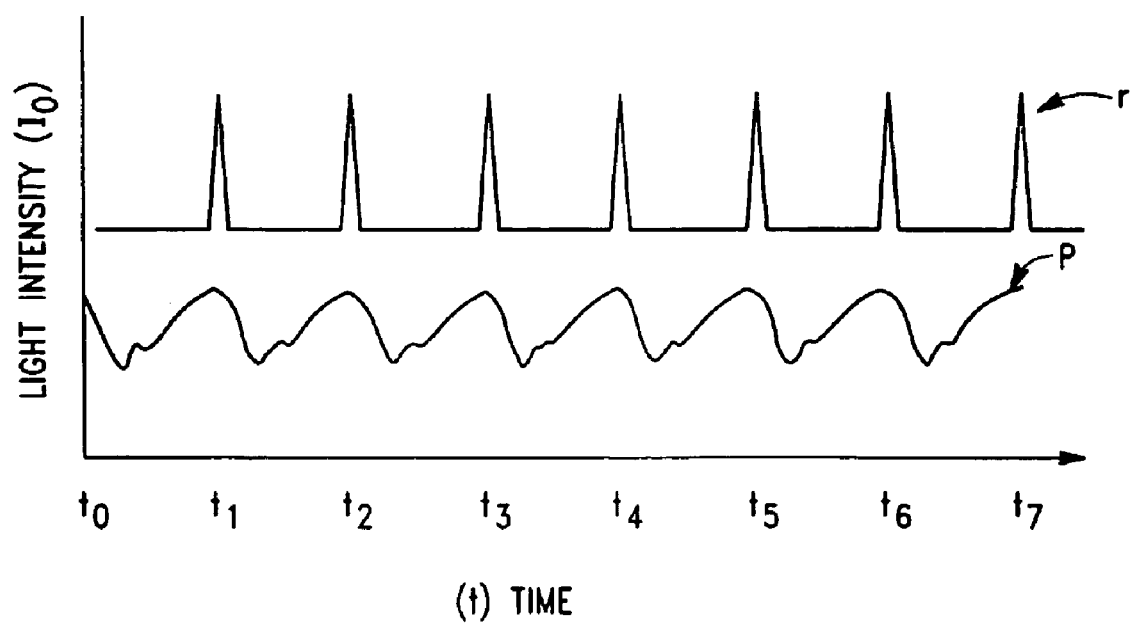
FIG. 1 is a graphical illustration of an r-wave portion of an electrocardiogram waveform and the related plethysmographic waveform.

Before describing the present invention in detail, it is to be understood that this invention is not limited to particularly exemplified materials, methods or structures as such may, of course, vary. Thus, although a number of materials and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a," "an" and "the" include plural referents unless the content clearly dictates otherwise.

Definitions

The term "signal", as used herein, is meant to mean and include an analog electrical waveform or a digital representation thereof, which is collected from a biological or physiological sensor.

The term "desired signal component", as used herein, is meant to mean and include the portion of a signal that directly corresponds to the biological or physiological function being monitored.

The term "motion artifact", as used herein, is meant to mean and include variability in a signal due to changes in the tissue being monitored that are caused by muscle movement proximate to the oximeter sensor.

The term "undesirable signal component", as used herein, is meant to mean and include any portion of a signal that does not correspond to the biological or physiological function being monitored. As such, the term includes, without limitation, noise, interference, and other variables that hinder the measurement of the biological or physiological function. Generally, motion artifacts are not the subject of this invention.

The terms "patient" and "subject", as used herein, is meant to mean and include humans and animals.

The present invention substantially reduces or eliminates the disadvantages and drawbacks associated with convention signal processing systems, apparatus and techniques. As discussed in detail below, a desired signal component is separated deliberately, analytically and specifically from an undesirable signal component using time dependent differences in signals derived from a single pulse. A combination of the amplitudes of two optical signals is used to correct the divergence between the signals, and thus estimate a residual signal that corresponds to the undesirable signal component.

In turn, the estimated residual signal is used to correct the optical signals. Thus, the invention provides a method for improving an oximetry signal based on analytical, mathematical steps that are analytically transparent, interpretable and adjustable on a physiological and physical level, and based on an understanding of the variables that interfere with oximetry signals, to optimally minimize specific interferences with the oximetry signal Preferably, the residual signal is estimated from data reflecting the highest signal to noise ratio. For oximetry data, the highest signal to noise ratio can be obtained by selecting data from time points corresponding to the maximal and minimal amplitudes of the plethysmographic waveform and from a time point corresponding to an analytical derivative of the maximum and minimum. Accordingly, the inventive analysis is based on specific time dependent differences in signal amplitude and can be performed using information from only three distinct time points of a single pulse wave. Further, by using values from the maximal and minimal amplitudes, the relative magnitude of the total oximetry signal is maximized, providing the best estimation of the undesirable signal component.

In one embodiment of the invention, the method and apparatus for processing signals reflecting a physiological characteristic generally comprises detecting the intensity of light following tissue absorption at two wavelengths and subtracting the best estimate of the desired signal from the difference between the signals.

As noted above, conventional pulse oximeters generate a composite oximetry signal that includes the desired signal component corresponding to the true oximetry component and an undesirable signal component reflecting noise, interference and variability. The undesirable signal components are estimated to comprise in the range of approximately 5 to 15% of the total signal. This invention provides a means for eliminating a substantial portion of the undesirable signal components in an easily implemented process that does not require the acquisition of additional signals. For the purposes of providing an improved oximetry measurement, it relatively unimportant to understand the exact sources of the undesired signal components so long as their effect can be removed or minimized.

Non-invasive pulse oximetry is based on a comparison of the absorption of red and infrared wavelengths. There is however no fundamental physiological reason for the red and infrared signals to vary from each other in their timing with respect to any given portion of a cardiac cycle. Accordingly, any measured difference can be attributed to interfering, undesirable signal components.

A conventional pulse oximeter generates a signal that is estimated to comprise as high as 90% desirable signal component. As demonstrated below, the invention involves subtracting the best estimate portion of the total signal from the difference between the red and infrared signals at every time and wavelength point. This reduces the undesirable signal components from approximately 10% to approximately 1%. Thus, the resulting corrected oximetry signal approaches 99% accuracy, improving the quality of the data several fold.

Referring first to FIG. 1, there is shown a graphical illustration of an "r-wave" portion of an electrocardiogram (ECG) waveform (designated "r") and the related plethysmographic waveform (designated "p"). As will be appreciated by one having ordinary skill in the art, the ECG waveform comprises a complex waveform having several components that correspond to electrical heart activity. The QRS component relates to ventricular heart contraction.

The r-wave portion of the QRS component is typically the steepest wave therein, having the largest amplitude and slope, and can be used for indicating the onset of cardiovascular activity. The arterial blood pulse flows mechanically and its appearance in any part of the body typically follows the R wave of the electrical heart activity by a determinable period of time that remains essentially constant for a given patient. See, e.g., Goodlin et al., Systolic Time Intervals in the Fetus and Neonate, Obstetrics and Gynecology, Vol. 39, No. 2, (February 1972) and U.S. Pat. No. 3,734,086.

Figure 2:
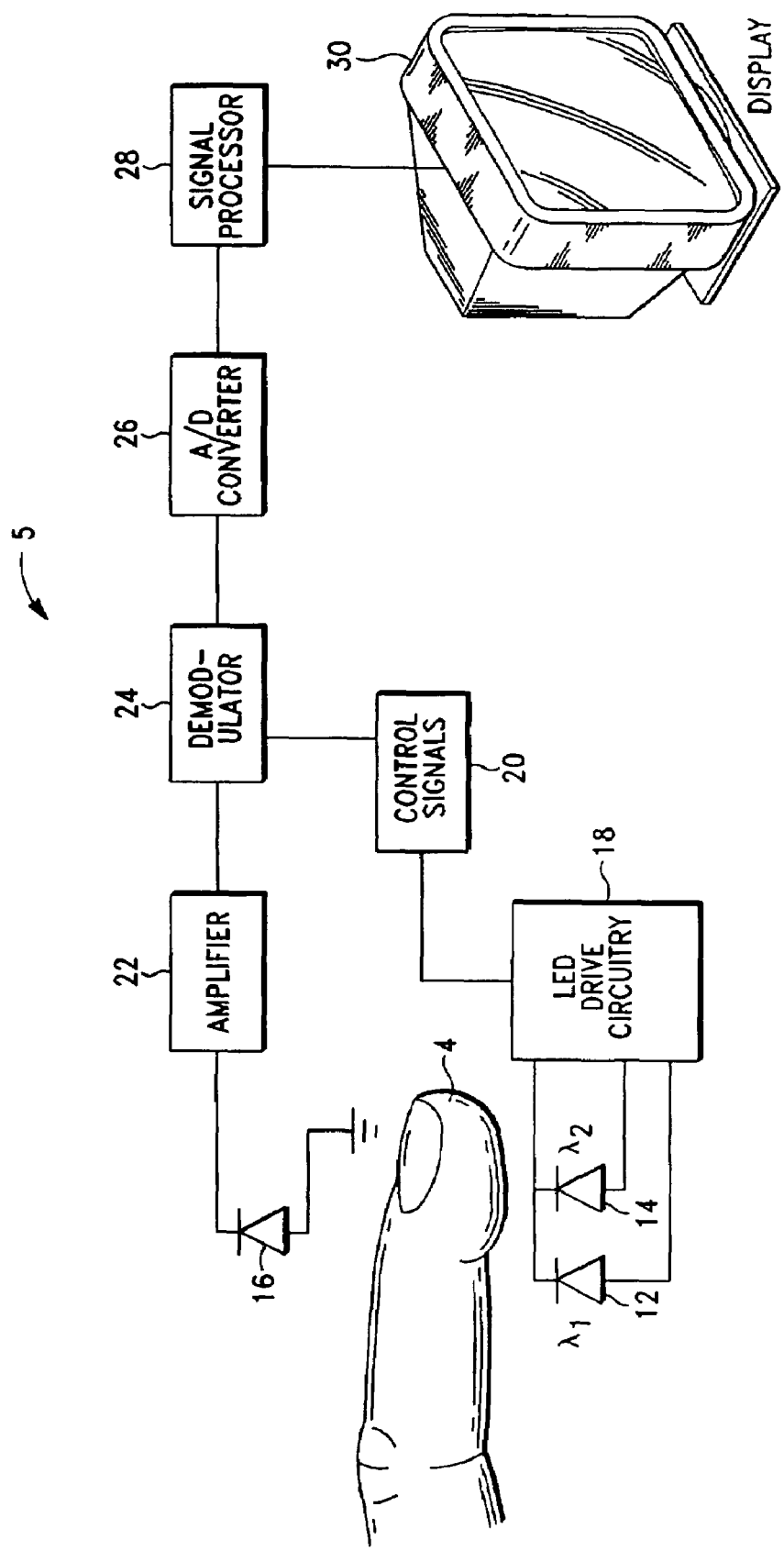
FIG. 2 is a schematic illustration of a pulse oximeter apparatus, according to the invention.

Referring now to FIG. 2, there is shown a schematic illustration of one embodiment of a pulse oximeter apparatus 5 that can be employed within the scope of the invention. As discussed above, conventional pulse oximetry methods and apparatus typically employ two lights; a first light having a discrete wavelength in the range of approximately 650–670 nanometers in the red range and a second light having a discrete wavelength in the range of approximately 800–1000 nanometers. For example, a suitable red LED emits light at approximately 660 nanometers and a suitable infrared LED emits light at approximately 880 nanometers.

The lights are typically directed through a finger 4 via emitters 12, 14 and detected by a photo detector 16, such as a square photodiode with an area of 49 mm$^2$. Emitters 12 and 14 are driven by drive circuitry 18, which is in turn governed by control signal circuitry 20. Detector 16 is in communication with amplifier 22. In one embodiment, the LEDs are activated at a rate of 8,000 times per second (8 kHz) per cycle, with a cycle comprising red on, quiescent, IR on, quiescent. In the noted embodiment, the total cycle time is 125 microseconds and the LEDs are active for approximately 41.25 microseconds at a time.

The photo detector 16 provides an output signal that is transmitted to an amplifier 22. The amplified signal from amplifier 22 is then transmitted to demodulator 24, which is also synched to control signal circuitry 20. As will be appreciated by one having skill in the art, the output signal from the demodulator 24 would be a time multiplexed signal comprising (i) a background signal, (ii) the red light range signal and (iii) the infrared light range signal.

The demodulator 24, which is employed in most pulse oximeter systems, removes any common mode signals present and splits the time multiplexed signal into two (2) channels, one representing the red voltage (or optical) signal and the other representing the infrared voltage (or optical) signal.

As illustrated in FIG. 2, the signal from the demodulator 24 is transmitted to analog-digital converter (ADC) 26. The desired computations are performed on the output from the converter 26 by signal processor (DSP) 28 and the results transmitted to display 30. In one embodiment, ADC 26 converts the analog signals into 16-bit signed digital signals at a rate of 8 kHz. Further, DSP 28 preferably notch filters the data at 40 Hz to eliminate power line frequency noise limit high frequency noise from other sources. Also preferably, the DSP then parses each data stream by a factor of 4 to give two digital data streams at a rate of 2 kHz.

Further details of the conventional pulse oximeter components, and related functions, are set forth in U.S. Pat. No. 4,934,372, which is incorporated by reference herein.

In one embodiment, the system electronics are configured such that emitters 12 and 14 are driven with a variable gain to produce an AC signal (corresponding to the photoplethysmograph pulse waveform) riding on a larger DC signal. The current supplied to the emitters is feedback driven to produce a constant DC signal of approximately 1.25 V, for both the red and infrared signals. The actual DC value is reported continuously. The magnitude of the AC signals is computed relative to the DC signal. The AC component is the signal that is given to the ADC 26 and converted to digital, with the DC signal treated as the "zero point". This creates a factor of the voltage range of the ADC 26 divided by the dynamic (digital) range of the DSP 28. As one having skill in the art will recognize, actual AC voltage level is computed by multiplying the digital AC counts are multiplied by the voltage conversion factor times the DC voltage.

As discussed above, a significant portion of optical pulse signals that are collected with conventional oximetry probes comprises a desired signal component, which is related to blood oxygen saturation. Indeed, it is estimated that approximately 85 to 95% of the entire optical pulse signal corresponds to desired signal component. The remaining approximately 5 to 15% of the composite signal comprises an undesirable signal component from highly variable combinations of sources.

The undesirable signal component chiefly corresponds to at least five categories. First, there is instrument-related electronic noise and drift. Second, there are low frequency components, in the range of approximately 0.1 to 10 Hz of variable amplitude, likely induced by variations in vasomotor control. Third, there is a variable excursion that appears to coincide with maximal blood pressure changes during the rise. This may represent a blood pressure change induced pressure wave propagating through tissue, which likely that such alters the ratio of absorbed to scattered radiation. Fourth, there are subject and site related irregularities. These include features such as skin thickness, scar tissue, lesions, bone density that could effect sensor output due to different time-dependent compression and relaxation effects. Finally, there are motion artifacts, which are not the focus of this invention.

As one having skill in the art will appreciate, a measurement of a subject's oxygen saturation would be significantly enhanced by removing the undesirable signal component before calculating the blood oxygen saturation. The resulting corrected oximetry data can be used in a conventional way, such as by relating the log ratio of optical maxima at the systole and optical minima at a diastole to reference oxygen saturation.

According to the invention, the average of the amplitude that is multiplied by a variable, "residual factor f," and subtracted from the difference in amplitude between the red and infrared signals corresponds to a residual signal reflecting the undesirable signal component. By correcting the amplitude of the red and infrared signal at each time point with this residual, a signal is generated that can be used to more accurately determine blood oxygen saturation.

Figure 3:
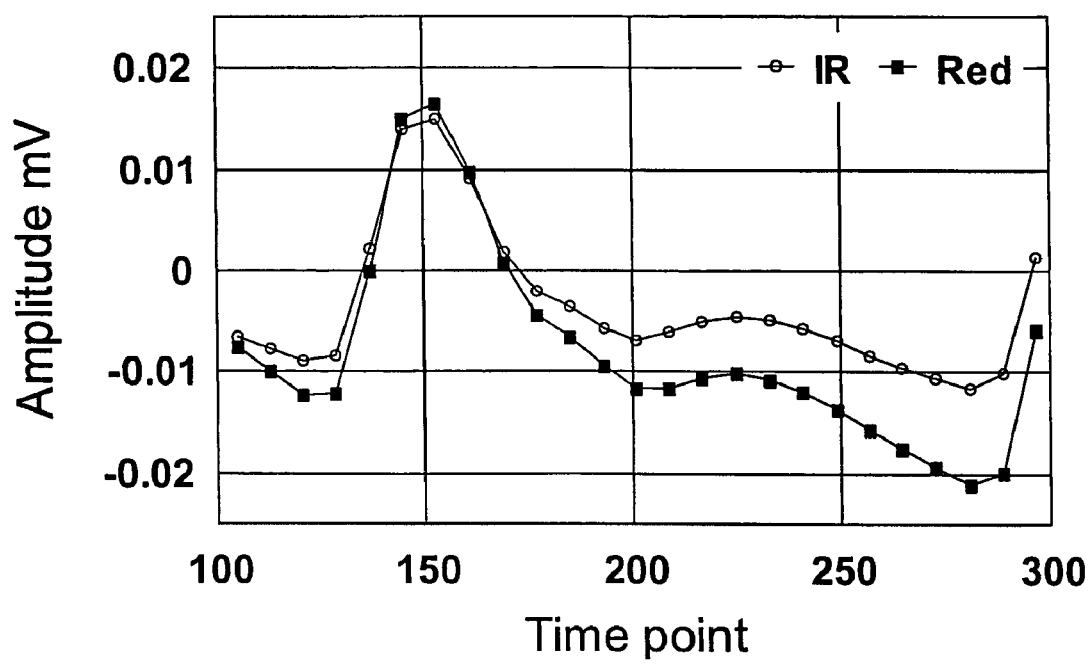
FIGS. 3 and 4 are graphical illustrations of red and infrared optical signals taken from independent sensors, according to the invention.
Figure 4:
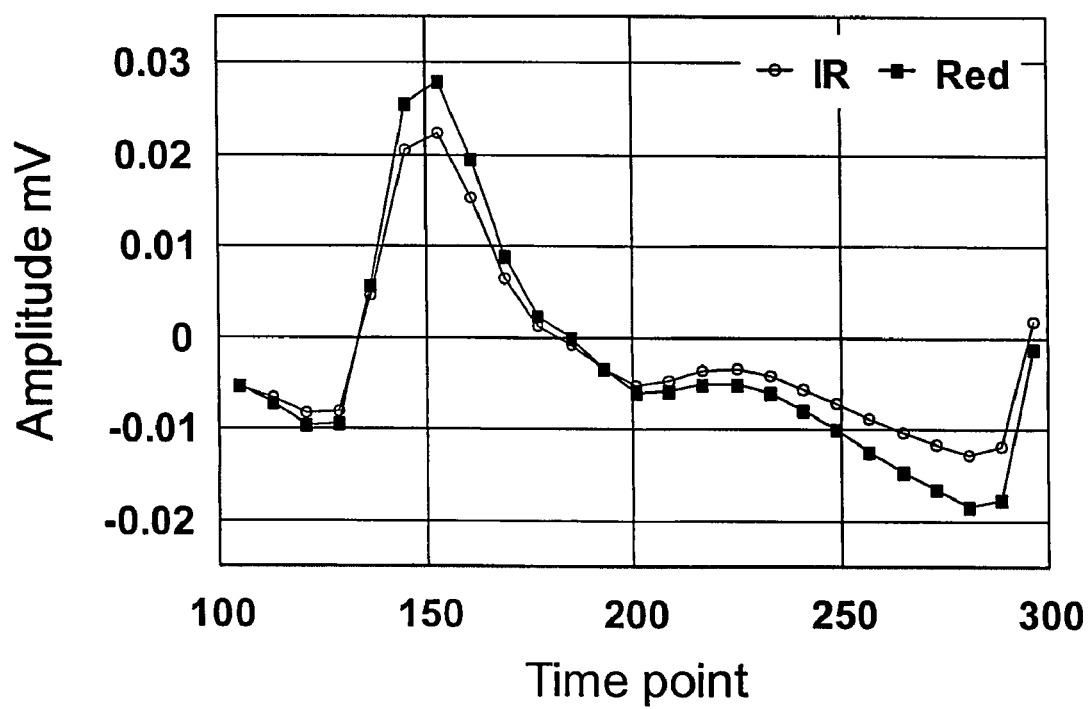

The specifics of this process are discussed below with respect to exemplary signal data obtained from pulse oximeter 5 using two independent sensors A and B, for example, one attached to the index finger of each hand of a subject. FIGS. 3 and 4 show data collected during a single pulse, from independent sensors A and B. In one embodiment, maximal and minimal amplitudes of the data streams are determined using a comparator on a continuous moving average of 50 samples. Depending upon the application, different sample rates can be used.

According to the invention, both outputs of sensor A are converted to amplitudes in mV, $A_{IR}$ and $A_{Red}$. The difference between these two amplitudes $A_{Diff}$ is $$A_{Diff} = A_{IR} - A_{Red}$$

and the average $A_{Avg}$ of these two absorbances is $$A_{Avg} = (A_{IR} + A_{Red})/2$$

Figure 5:
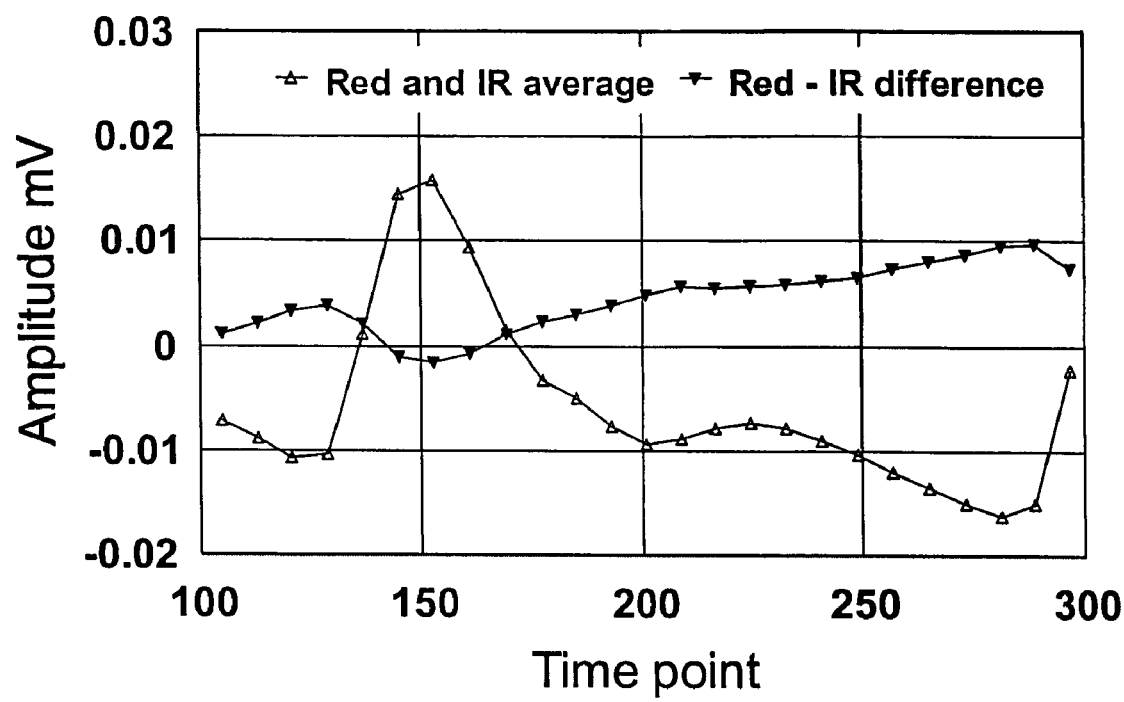
FIGS. 5 and 6 are graphical illustrations of amplitude averages and differences of the red and infrared optical signals taken from the independent sensors, according to the invention.
Figure 6:
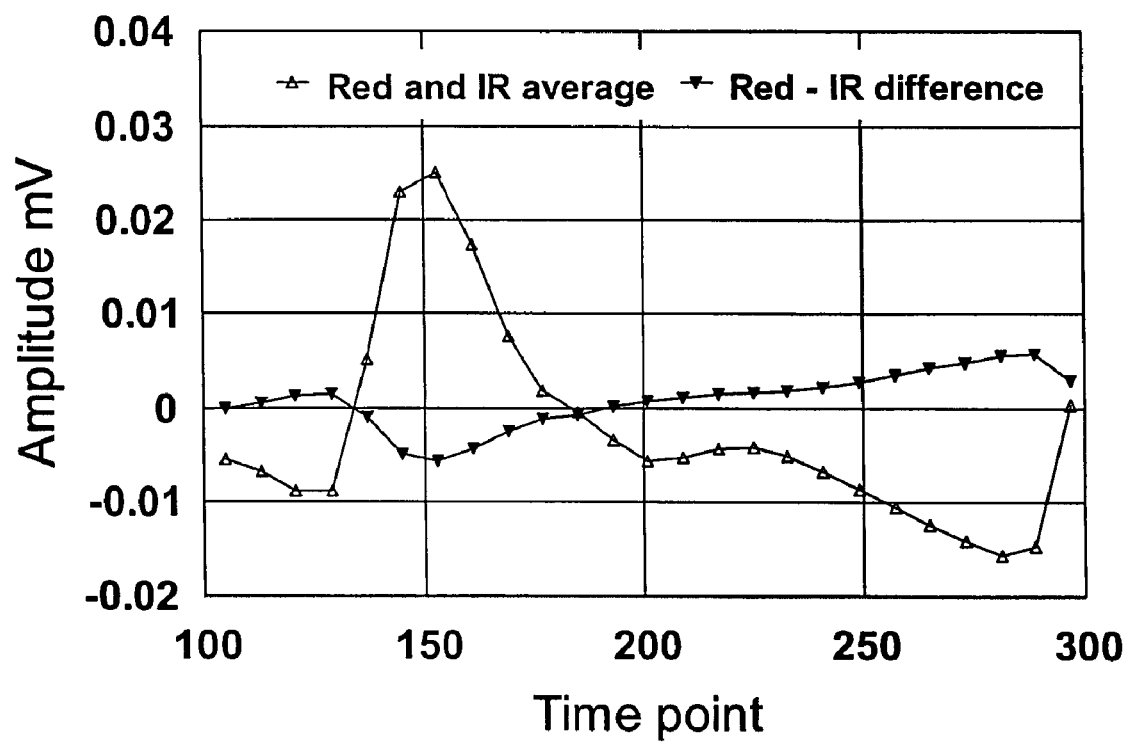

Preferably, all calculations are done at all time points of the chosen pulse. The corresponding generated signals $A_{Diff}$ and $A_{Avg}$ from sensor A and sensor B are shown in FIGS. 5 and 6, respectively.

The desired signal component is then estimated and subtracted from the total signal until there is no detectable oximetry signal detectable in the residual. At this point, the residual corresponds to the undesirable signal components. Therefore, the variable, "residual factor f," is used as a multiplier for $A_{Avg}$ and the product is subtracted from $A_{Diff}$ to obtain corrected absorbance difference, or $$A_{DiffCorr} = A_{Diff} - (f * A_{Avg})$$

which is free of the optical oximetry signal.

In the noted embodiment, an average of the infrared and red signals is used because there is no specific basis for determining which signal is affected more by undesirable signal components. In alternative embodiments, different combinations of the two signals can be used. For example, if it were expected that the red signal was more affected than the infrared signal a combination that weighted the red signal more heavily would be desirable.

The residual factor f is preferably advanced in small increments such as 0.01 from −1 to +1. As the residual factor is advanced, at a value that depends on saturation, one can visually observe the typical oximetry pulse wave signal as a component of the residual become smaller, go through the remaining residual at every time point of the $A_{DiffCorr}$ and become the negative mirror image as it grows in the opposite direction. Thus, there is a value of f at which the entire measured oximetry component is removed and the residual is by default the sum of the undesirably signal components.

According to the invention, the residual factor f can thus not only be used for correction of the original waveform, but also for calibration purposes of the oximeter signal after removal of undesirable signal component. The residual factor f can additionally be calibrated against reference CO-oximeter data and serve as the operating parameter for pulse oximetry.

According to the invention, it is desirable to determine residual factor f using data when the oximetry signal has a high signal to noise ratio. This can be achieved by selecting time points that correspond to maximal and minimal amplitudes of the plythesmographic waveform. Thus, averages of amplitude signals of $A_{DiffCorr}$ can be calculated at the minimum, shown in FIGS. 5 and 6 between time points 124 and 126, and at the maximum, shown in FIGS. 5 and 6 between time points 158 and 160. As described above, the maximal and minimal amplitudes are readily determined using a comparator. The time mid-point is the arithmetic mean between the time point at the maximum and the time point at the minimum, ((time point at max+time point at min)/2).

Preferably, the first data minimum in a selected pulse is used, because this minimum occurs more closely to the maximal amplitude and is therefore less affected by any drift in the instrument. As shown in FIGS. 5 and 6, the time midpoint occurs at time point 142. The average signal amplitude is calculated from the values at time points 141 to 143. In this manner, the amplitudes of $A_{DiffCorr}$ are known at the first data minimum, the first data maximum (later maxima are ignored) and at the data midpoint.

In other embodiments of the invention, an average of the first data minimum and a second data minimum can be used. The second minimum at the end of the current pulse is the lowest amplitude occurring between the current pulse and the succeeding pulse. Alternatively, the plethysmographic waveform can have a relatively long flat portion that corresponds to a minimum value. In these circumstances, averaging the value of the curve in that portion can provide a suitable value for the analysis.

Additionally, baseline adjustment can be used to remove specific noise prior to the steps described here. Baseline adjustment is well known in many applications of spectroscopy and hence, is not further described herein. The beneficial effect of this additional step is small in most cases.

According to the invention, it can be more accurate to identify the time points by curve fitting the maximum and minimum sections, especially with noisy data. In these alternate embodiments, polynomial fits over a time-variable section of the red and infrared data are preferred for determining the exact time points. As the heart rate is highly variable, a more accurate approach for finding the optimal time section for fitting can be to define the fitted section by the time it takes for the amplitude to change by a significant percentage, e.g., two percent (2%). In such embodiments, a curve fit through the midpoint can also include more time points.

In a preferred embodiment, two qualifiers are defined to determine residual factor f for any given pulse. The qualifiers are selected to provide an optimal estimation of the residual based upon the physiological and physical characteristics of the oximetry measurement. Preferably, these qualifiers are equal to at least four decimals, and more preferably, to six or better, such that the current undesirable signal components dominate the residual $A_{DiffCorr}$.

Qualifier 1 (Q1) is the difference of the absolute value of the amplitude of the residual at time midpoint, also referred to as $A_{DiffCorrMid}$ and the average of the amplitudes of the residuals at the first data minimum ($A_{DiffCorrMin}$) and the residual at the first data maximum ($A_{DiffCorrMax}$):

$$Q1 = |A_{DiffCorrMid} - ((A_{DiffCorrMin} + A_{DiffCorrMax})/2)|$$

Qualifier 2 (Q2) is the absolute difference of the amplitude at the first data maximum and the amplitude at the first data minimum:

$$Q2 = |A_{DiffCorrMin} - A_{DiffCorrMax}|$$

In one embodiment, Q1 is employed such that the residual factor f can be determined from data collected at a minimum of three discrete timepoints, i.e., the first data maximum, the first data minimum and the data midpoint. The derived correction can then be applied to all timepoints of the pulse. In an alternate embodiment, Q2 is employed.

Preferably, both Q1 and Q2 are minimized simultaneously to reflect maximum suppression of the pulse oximetry content in the residual. Residual factor f is varied until the difference between the qualifiers approaches zero. For example, f can be set to 1 and then decreased towards −1 in increments. Depending upon the computation power of the instruments used, the increment can range from approximately 0.1 to 0.000001. Preferably, the value for f that produces the smallest difference between the two qualifiers is then used to determine the residual at all time points.

Figure 7:
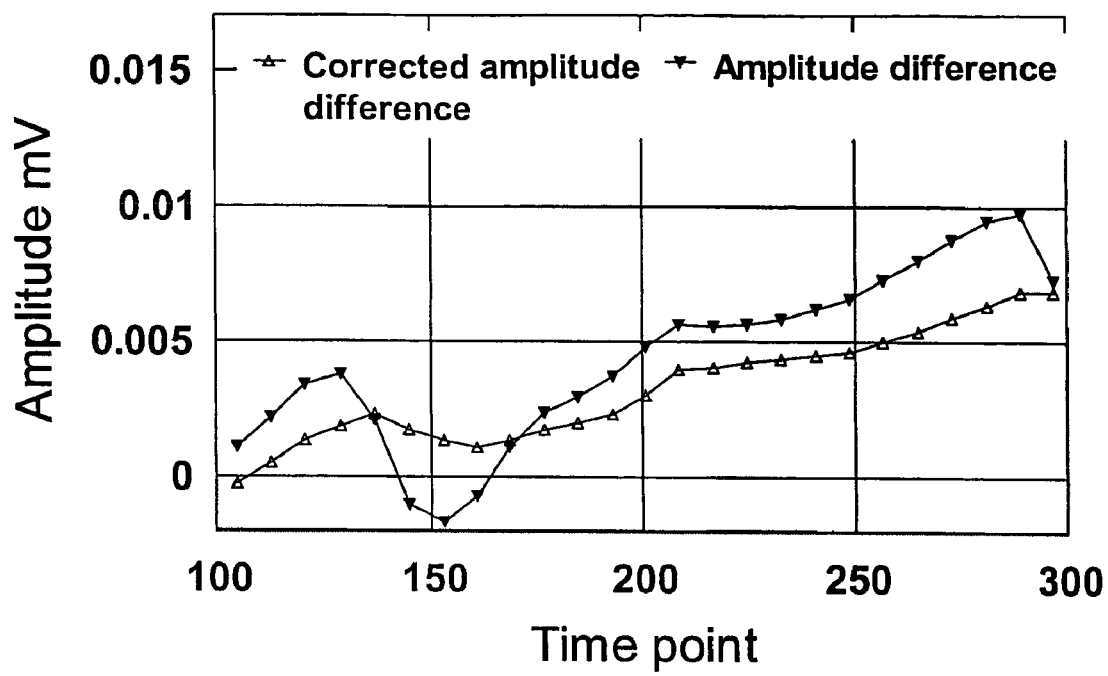
FIGS. 7 and 8 are graphical illustrations of amplitude differences and corrected amplitude differences of the red and infrared optical signals taken from the independent sensors, according to the invention.
Figure 8:
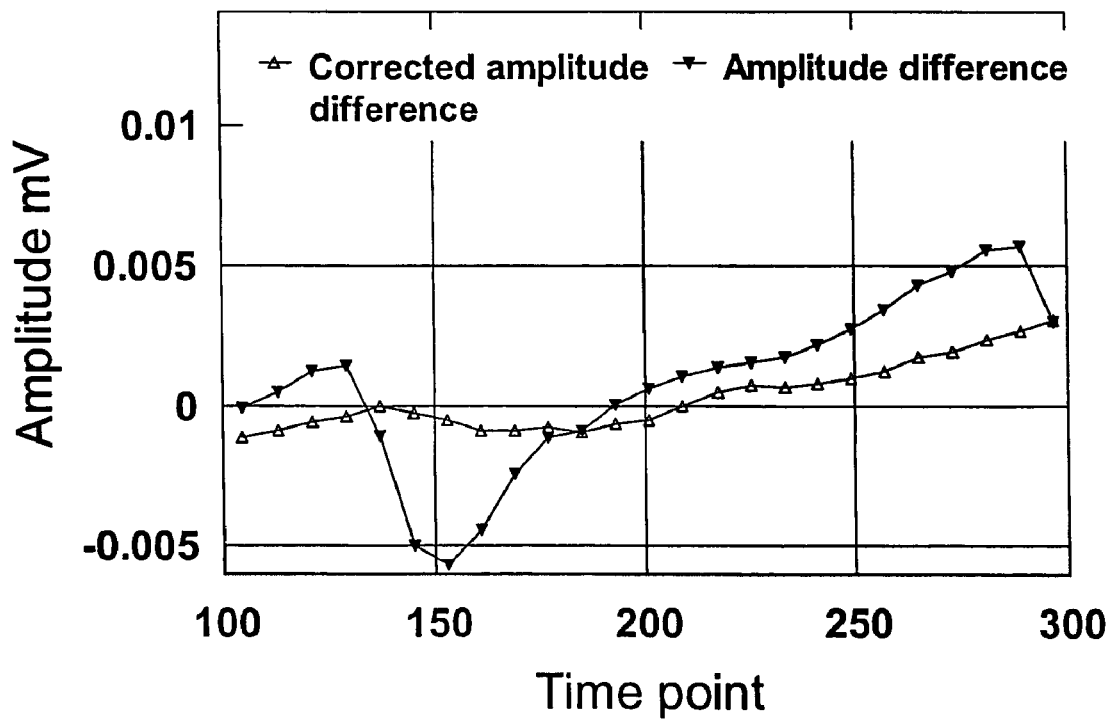

Turning to FIGS. 7 and 8, $A_{Diff}$ and $A_{DiffCorr}$ are shown for the data obtained from sensors A and B, respectively. As can be seen, common features in the optical signal that correlate to changes in blood pressure appear in $A_{Diff}$, but not in $A_{DiffCorr}$. For example, the pulse maximum occurring around time point 150 is no longer recognizable in the residual, $A_{DiffCorr}$. Accordingly, the residual corresponds to undesirable signal components and does not reflect the pulse oximetry signal.

As discussed above, in a preferred embodiment of the invention, residual factor f is chosen by minimizing Q1 and Q2. As can be seen in FIGS. 7 and 8, $A_{DiffCorr}$ is not necessarily flat between the first data minimum and maximum. Thus, minimizing the difference of the residuals between these points does not represent an optimal solution. Since there is curvature and slope in the residual, the deviation of the mean value of the actual residual from the arithmetic mean needs to be minimized to provide the best estimation of residual factor f.

By deriving this residual value, the sum of components that are unrelated to pulse oximetry are quantitatively determined within the limits of instrument noise in the data. Corrected amplitudes can thus be determined by calculating, at all time points during the pulse, the best estimate of the true oximetry components as $$A_{IRCorr} = A_{IR} - (A_{DiffCorr}/2)$$

and $$A_{RedCorr} = A_{Red} + (A_{DiffCorr}/2)$$

Figure 9:
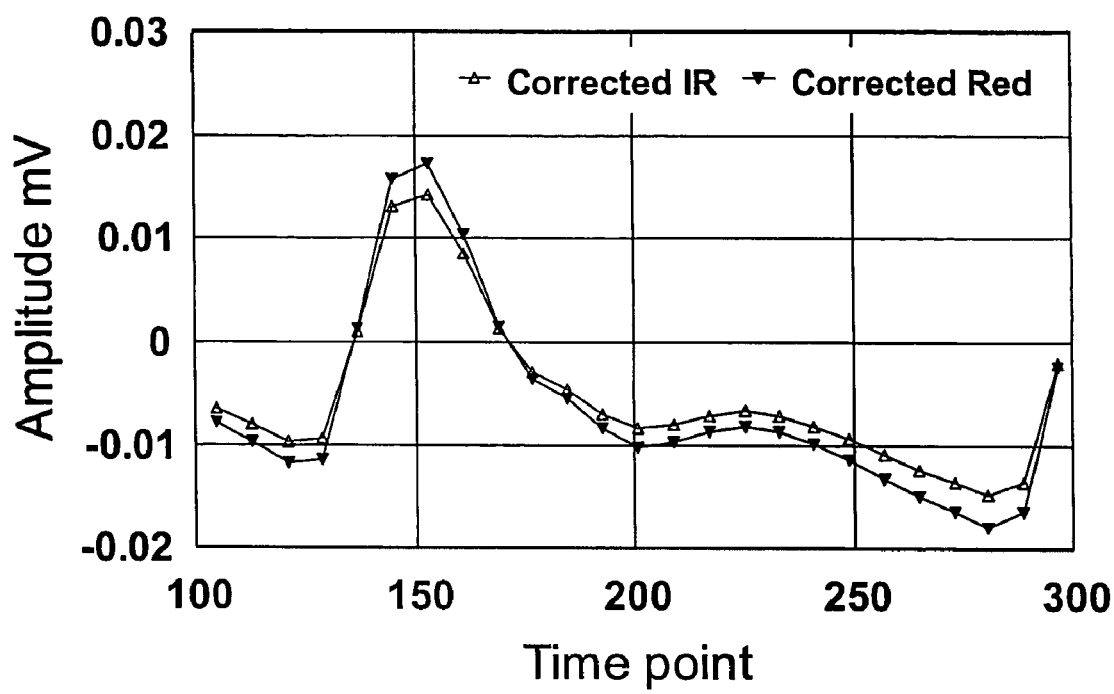
FIGS. 9 and 10 are graphical illustrations of the corrected amplitudes of the red and infrared optical signals taken from the independent sensors, according to the invention.
Figure 10:
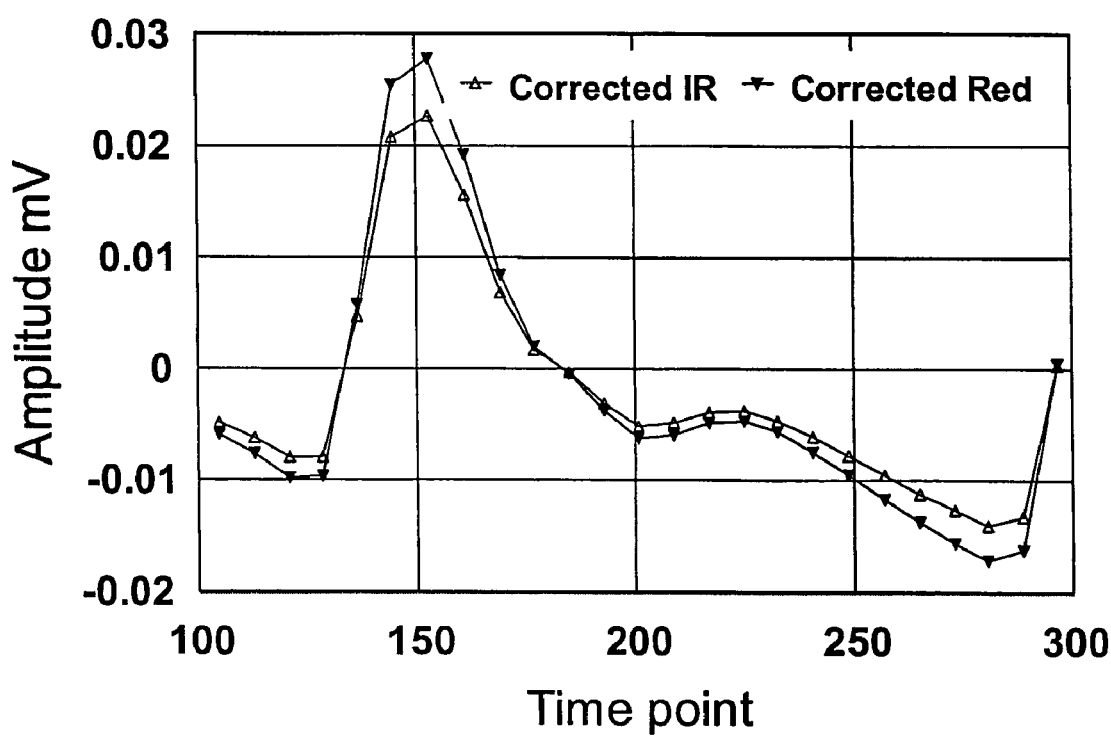

Turning now to FIGS. 9 and 10, the signals $A_{IRCorr}$ and $A_{RedCorr}$ are shown for the data collected from sensors A and B, respectively. As one having skill in the art will readily recognize, there may still be low frequency drift of the corrected red and infrared oximetry signals. Different first and second minima of different pulses demonstrate this effect. However, this invention provides predictable oximetry information at every time point during every pulse.

The above calculations are performed on data derived from three discrete timepoints during a specific pulse. The residual calculated from these timepoints is then applied to each timepoint of the pulse. In this manner, all the required information is obtained during a single pulse. In contrast to prior art methods of improving pulse oximetry signals, there is no requirement to fit the data to preselected pulse waveforms or to derive a pulse waveform based on preceding pulses.

According to the invention, the corrected amplitudes $A_{IRCorr}$ and $A_{RedCorr}$ can be used to calculate a ratio of logarithms, the principal measurement parameter related to reference saturation percent for calibrating pulse oximeters. First, the amplitudes of $A_{RedCorrMin}$ and $A_{IRCorrMin}$, which represent the equivalent of optical transmittance, are brought to zero. In one embodiment, this step is performed at the first data minimum. More preferably, this step is performed at the average of the first and the second data minimum. The ratio R is then calculated as the absolute logarithm of the zeroed red amplitude over the absolute logarithm of the zeroed infrared amplitude:

$$R = |(\log(A_{RedCorr} - A_{RedCorrMin}))|/|(\log A_{IRCorr} - A_{CorrMin}))|$$

The resulting ratio R is then related to the reference oxygen saturation conventionally.

Preferably, Q1 and Q2 are tailored for the specific conditions associated with pulse oximetry and the nature of the variables that interfere with the acquisition of pure oximetry signals. Other qualifiers can be developed, modified and/or adjusted to optimize the determination of residual factor f depending upon the biological or physiological characteristic being measured and the nature of the interfering variables. For example, other analytically derived time points between the maximum and minimum amplitudes can be used.

EXAMPLES

The following examples are given to enable those skilled in the art to more clearly understand and practice the present invention. They should not be considered as limiting the scope of the invention, but merely as being illustrated as representative thereof.

Example 1

Figure 11:
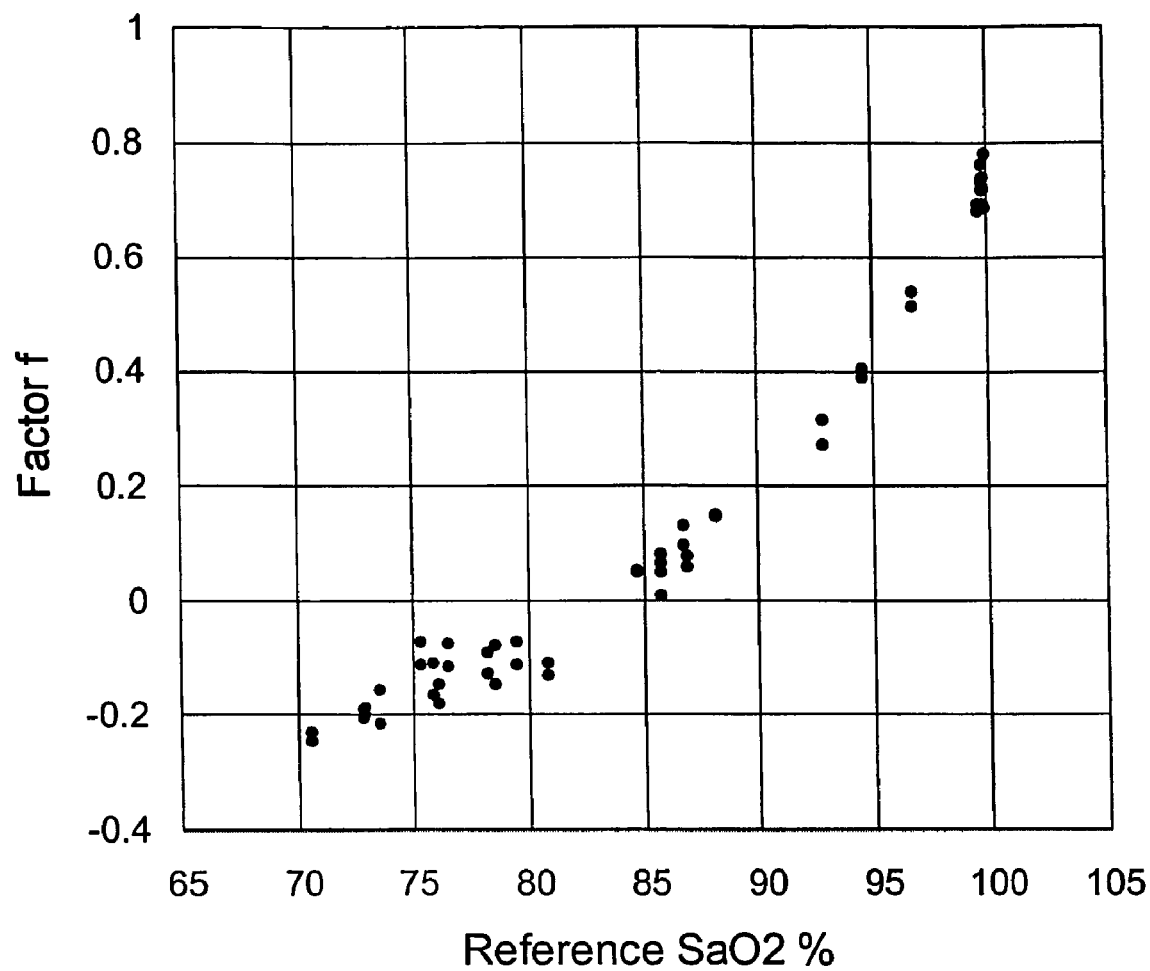
FIG. 11 is a graphical illustration of the residual factor f used to correct the red and infrared optical signals as a function of oxygen saturation, according to the invention.

Desaturation studies of seven human subjects were performed and 53 independent data points corresponding to single pulses were collected. Values for residual factor f were derived using the steps described above and reference oxygen saturation was measured independently by a CO-oximeter instrument. As shown in FIG. 11, there is a close correlation between residual factor f and oxygen saturation. Correspondingly, residual factor f can serve as a basis for calibrating pulse oximeters in place of conventional ratios of logarithms.

Example 2

A study comparing oximetry determinations using data corrected as described above to reference oxygen saturation was performed with 8 adult volunteers. For the study, a catheter was placed into a radial artery of each subject. A Nellcor N-200 pulse oximeter was used as a reference device, and also for clinically monitoring the subject. Each subject was given varying inspired concentrations of oxygen in order to produce arterial hemoglobin oxygen saturations in the approximate range of 70–100%. Blood samples were drawn from the arterial catheter simultaneously with readings of oxygen saturation, and immediately analyzed. Data were collected of both the waveform being analyzed, as well as computed intermediate steps. The arterial blood sample was analyzed on two separate blood-gas analyzers by Radiometer. The functional saturation of hemoglobin was computed as oxyhemoglobin/(total hemoglobin). That is, all non-oxyhemoglobin species were included in total hemoglobin. At all saturations and for all human study subjects, the reference values for the algorithmically computed values were the average readings from two CO-oximeters.

Figure 12:
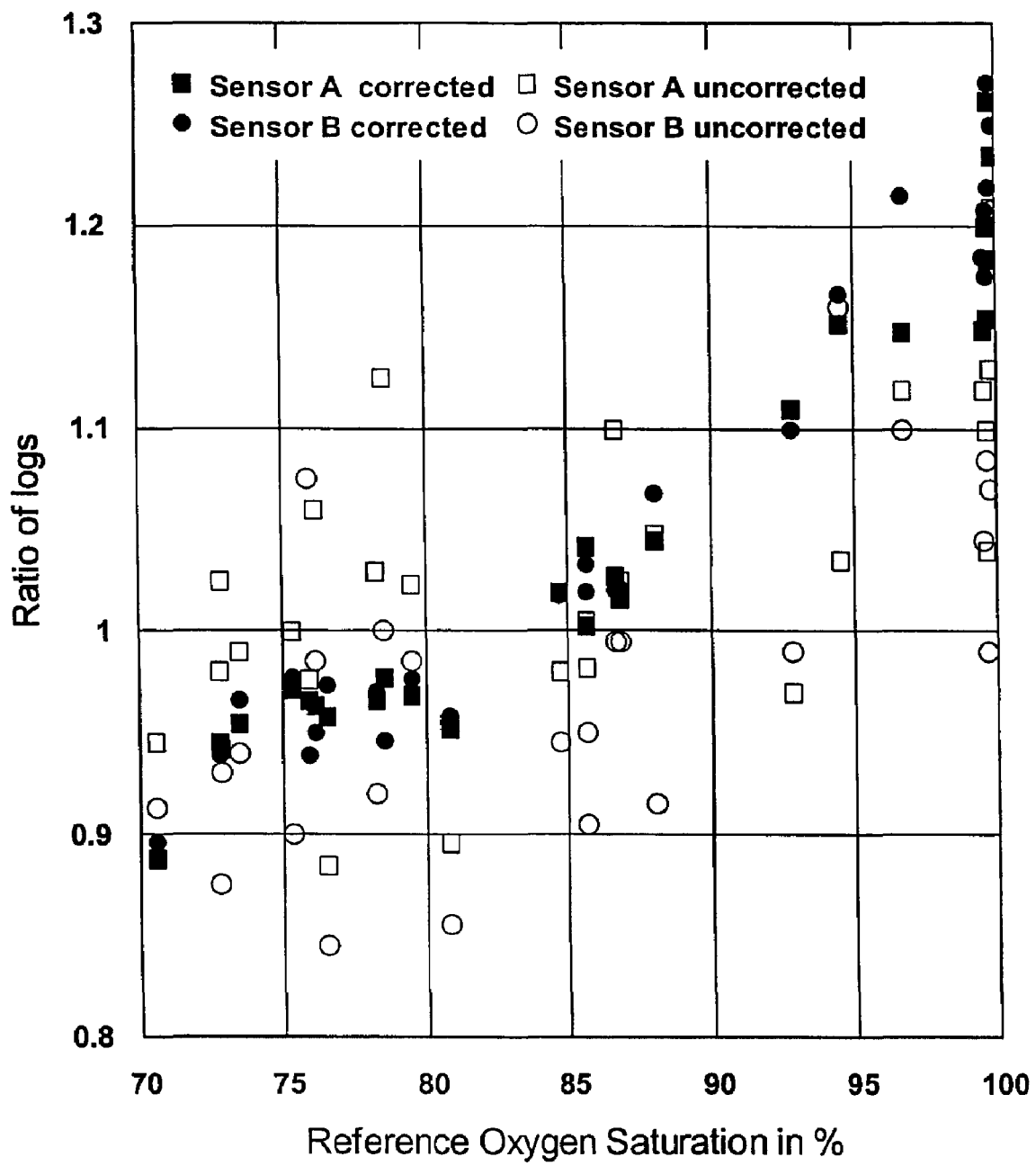
FIG. 12 is a graphical illustration comparing the corrected data of the red and infrared optical signals taken from the independent sensors to the uncorrected data, according to the invention.

FIG. 12 shows the results obtained from 26 independent measurements of the same pulse with two sensors, for a total of 52 measurements. The corrected and uncorrected data points are plotted on a graph relating the ratio of logarithms to oxygen saturation. As can be seen, the corrected signals represent much greater accuracy. Specifically, the process described above provided a 10.6 fold improvement as compared to the uncorrected values. Even when discarding the two highest improvement values, a 6.5 fold improvement is still obtained. Accordingly, in this experiment, the present invention offers a minimum of a six-fold improvement over conventional pulse oximetry without the requirement of acquiring any additional data.

In additional embodiments, the principles represented by the present invention can also be applied to a wide variety of other biological and physiological determinations. For example, U.S. Pat. Nos. 6,480,729, 6,537,225, 6,594,511, 6,719,705, 6,819,950, and 6,921,367 and U.S. application Ser. No. 10/912,721, filed 4 Aug. 2004, all of which are incorporated in their entirety by reference, each relate to the acquisition of signals for determining physiological characteristics and can be practiced with the methods and apparatus of the present invention.

Without departing from the spirit and scope of this invention, one having ordinary skill in the art can make various changes and modifications to the invention to adapt it to various usages and conditions. As such, these changes and modifications are properly, equitably, and intended to be, within the full range of equivalence of the following claims.

What is claimed is:

1. A device for the monitoring of a physiological characteristic of a patient's blood, comprising:

a first radiation emitter that emits light at a first wavelength;

a second radiation emitter that emits light at a second wavelength;

a radiation detector configured to receive light at said first and second wavelengths after absorbance through the patient's blood and provide a first intensity signal and a second intensity signal corresponding to said first and second received wavelengths; and a controller for computing said physiological characteristic of said patient's blood from a corrected first intensity signal and a corrected second intensity signal determined by applying a residual derived from a combination of said first and second intensity signals as multiplied by a residual factor and subtracted from a difference between said first and second intensity signals to said first and second intensity signals.

2. The device of claim 1, wherein said physiological characteristic is arterial oxygen saturation.

3. The device of claim 2, wherein said first wavelength is in the range of approximately 650–670 nm.

4. The device of claim 2, wherein said second wavelength is in the range of 800 –1000 nm.

5. The device of claim 1, wherein said residual factor is determined by minimizing the absolute value of the difference between said residual at a time midpoint and an average of said residual at a first data minimum and at a first data maximum.

6. The device of claim 1, wherein said residual factor is determined by minimizing the absolute value of the difference of said residual at a first data maximum and said residual at a first data minimum.

7. The device of claim 6, wherein said first data minimum and said first data maximum are determined by polynomial fitting.

8. The device of claim 1, wherein said residual factor is related to reference oxygen saturation to determine said physiological characteristic.

9. The device of claim 1, wherein a ratio of said corrected intensity signals is related to reference oxygen saturation to determine said physiological characteristic.

10. The device of claim 1, wherein said residual is substantially free of a signal related to said physiological characteristic.

11. The device of claim 1, wherein said residual substantially corresponds to undesirable signal components.

12. A method for processing signals reflecting a physiological characteristic of a patient's blood, comprising the steps of:

coupling an oximeter sensor arrangement to a tissue region of said patient;

passing first and second lights through said patient's tissue region, wherein said first light is substantially in a red light range and said second light is substantially in an infrared light range;

detecting said first and second lights absorbed by said tissue region and providing a first intensity signal and a second intensity signal corresponding to absorbed first and second lights; and computing said physiological characteristic of said patient's blood from a corrected first intensity signal and a corrected second intensity signal determined by applying a residual derived from a combination of said first and second intensity signals as multiplied by a residual factor and subtracted from a difference between said first and second intensity signals to said first and second intensity signals.

13. The method of claim 12, wherein said physiological characteristic is arterial oxygen saturation.

14. The method of claim 12, wherein said residual factor is determined by minimizing the absolute value of the difference between said residual at a time midpoint and an average of said residual at a first data minimum and at a first data maximum.

15. The method of claim 12, wherein said residual factor is determined by minimizing the absolute value of the difference of said residual at a first data maximum and said residual at a first data minimum.

16. The method of claim 15, wherein said first data minimum and said first data maximum are determined by polynomial fitting.

17. The method of claim 12, wherein said residual factor is related to reference oxygen saturation to determine said physiological characteristic.

18. The method of claim 12, wherein a ratio of said corrected intensity signals is related to reference oxygen saturation to determine said physiological characteristic.

19. The method of claim 12, wherein said residual is substantially free of a signal related to said physiological characteristic.

20. The method of claim 12, wherein said residual substantially corresponds to undesirable signal components.

21. The method of claim 12, wherein said residual factor is determined by minimizing a qualifier.

22. The method of claim 21, wherein said qualifier is selected to correspond to said physiological characteristic.

23. A method for determining a patient's arterial oxygen saturation comprising the steps of:

coupling an oximeter sensor arrangement to a tissue region of said patient;

passing first and second lights through said patient's tissue region, wherein said first light is substantially in a red light range and said second light is substantially in an infrared light range;

detecting said first and second lights absorbed by said tissue region and providing a first intensity signal and a second intensity signal corresponding to said absorbed first and second lights; and computing said arterial oxygen saturation of said patient's blood from a corrected first intensity signal and a corrected second intensity signal determined by applying a residual derived from a combination of said first and second intensity signals as multiplied by a residual factor and subtracted from a difference between said first and second intensity signals to said first and second intensity signals, wherein said residual factor is determined by minimizing the absolute value of the difference between said residual at a first timepoint of a pulse corresponding to a time midpoint and an average of said residual at a second timepoint of said pulse corresponding to a first data minimum and at a third timepoint of said pulse corresponding to a first data maximum.

* * * * *